US00PP30655P2

(12) United States Plant Patent
Prukngen

(10) Patent No.: US PP30,655 P2
(45) Date of Patent: Jul. 2, 2019

(54) ***CANNA* PLANT NAMED 'RED TIGER'**

(50) Latin Name: ***Canna* x *generalis***
Varietal Denomination: Red Tiger

(71) Applicant: Brian's Botanicals, Louisville, KY (US)

(72) Inventor: Somchai Prukngen, Bangkok (TH)

(73) Assignee: BRIAN'S BOTANICALS, Louisville, KY (US)

( * ) Notice: Subject to any disclaimer, the term of this patent is extended or adjusted under 35 U.S.C. 154(b) by 0 days.

(21) Appl. No.: 15/932,848

(22) Filed: May 8, 2018

(51) Int. Cl.
*A01H 5/02* (2018.01)

(52) U.S. Cl.
USPC ..... Plt./415

(58) Field of Classification Search
USPC ..... Plt./263.1, 415
See application file for complete search history.

*Primary Examiner* — Susan McCormick Ewoldt
*Assistant Examiner* — Karen M Redden
(74) *Attorney, Agent, or Firm* — Penny J. Aguirre

(57) ABSTRACT

A new cultivar of *Canna* plant named 'Red Tiger' that is characterized by its compact and mid-sized plant habit, its flowers that are bright scarlet in color, its striated (variegated) foliage with alternating striations of green and yellow and a thin yellow margin, its petioles that are green with a yellow margin with the apex of the petiole variable striped, and inflorescences with 12 to 20 flower buds and typically with 3 to 4 flowers that are open at one time.

2 Drawing Sheets

Botanical classification: *Canna* x *generalis*.
Cultivar designation: 'Red Tiger'.

BACKGROUND OF THE INVENTION

The present invention relates to a new and distinct cultivar of *Canna* x *generalis* known as 'Red Tiger', and is hereinafter referred to as 'Red Tiger'. 'Red Tiger' is a new cultivar of *Canna* lily, which is grown as an annual or perennial depending on climate zone and for use in containers and in the landscape.

The new cultivar arose from an ongoing breeding program by the Inventor in Bangkok, Thailand with the goal of developing new cultivars of *Canna* with unique flower colors combined with yellow striated foliage.

The new cultivar was derived from a cross made by the Inventor in July of 2014 between unnamed and unpatented proprietary plants of *Canna* x *generalis* from the Inventor's breeding program as both the female and male parents. 'Red Tiger' was selected as a single unique plant from amongst the seedling that arose from the above cross in October of 2015.

Asexual reproduction of the new cultivar was first accomplished by rhizome division by the Inventor in Bangkok, Thailand in June of 2016. Asexual reproduction of the new cultivar by rhizome division has shown that the unique characteristics of 'Red Tiger' are stable and reproduced true to type in successive generations.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date.

SUMMARY OF THE INVENTION

The following traits have been repeatedly observed and represent the characteristics of the new cultivar. These attributes in combination distinguish 'Red Tiger' as a new and unique cultivar of *Canna*.

1. 'Red Tiger' exhibits a compact and mid-sized plant habit.
2. 'Red Tiger' exhibits flowers that are bright scarlet in color.
3. 'Red Tiger' striated (variegated) foliage with alternating striations of green and yellow and a thin yellow margin.
4. 'Red Tiger' exhibits petioles that are green with a yellow margin with the apex of the petiole variable striped.
5. 'Red Tiger' exhibits inflorescences with 12 to 20 flower buds and typically 3 to 4 flowers that are open at one time.

Both parents of 'Red Tiger' are similar to 'Red Tiger' in having compact and mid-sized plant habits and in having yellow and green striated foliage. The female plant of 'Red Tiger' differs from 'Red Tiger' in having flowers that are orange in color. The male plant of 'Red Tiger' differs from 'Red Tiger' in having flowers that are dull red in color. 'Red Tiger' can be most closely compared to the cultivars 'Bengal Tiger' and 'Minerva' (both unpatented). Both are similar to 'Red Tiger' in having yellow and green striated foliage. 'Bengal Tiger' differs from 'Red Tiger' in having a taller plant height and in having flowers that are orange in color with a yellow edge. 'Minerva' differs from 'Red Tiger' in having flowers that are bright yellow in color.

BRIEF DESCRIPTION OF THE DRAWINGS

The accompanying colored photographs illustrate the overall appearance and distinct characteristics of the new *Canna*. The photographs were taken of a 1-year-old plant as grown in a greenhouse in a 2-gallon container in Bangkok, Thailand.

Figure 1:
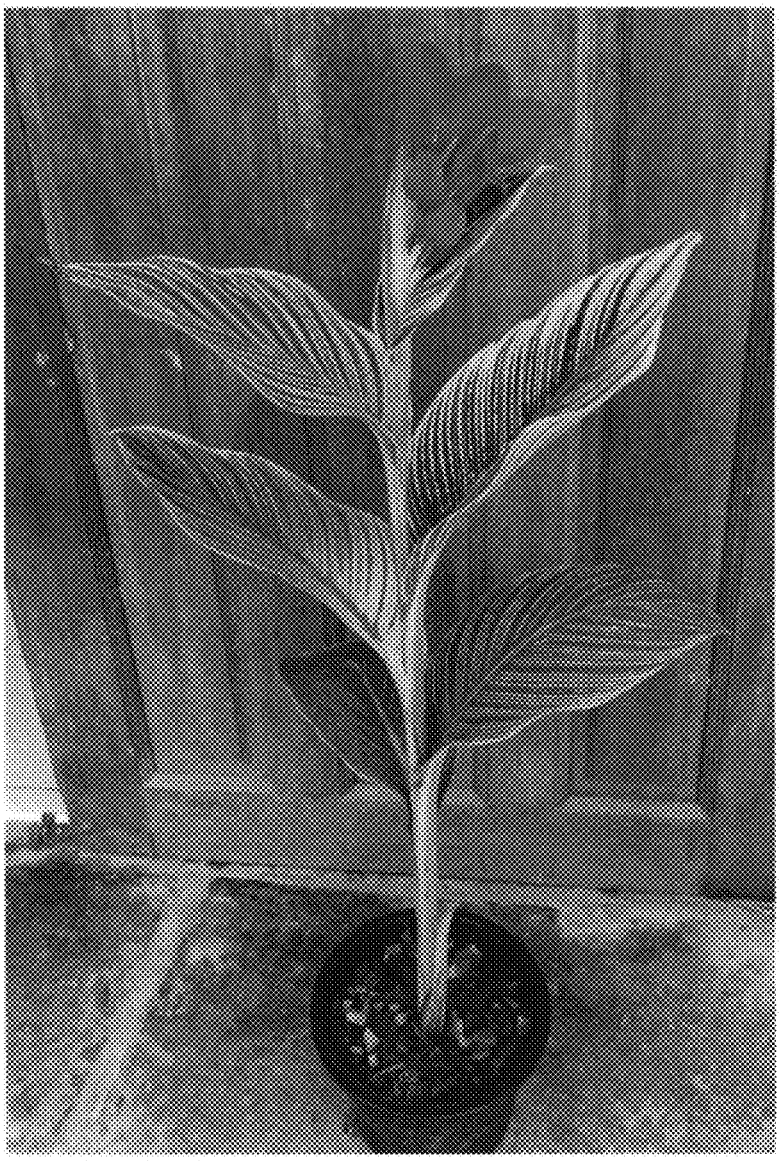
FIG. 1 provides a side view of a plant of 'Red Tiger' in bloom.
Figure 2:
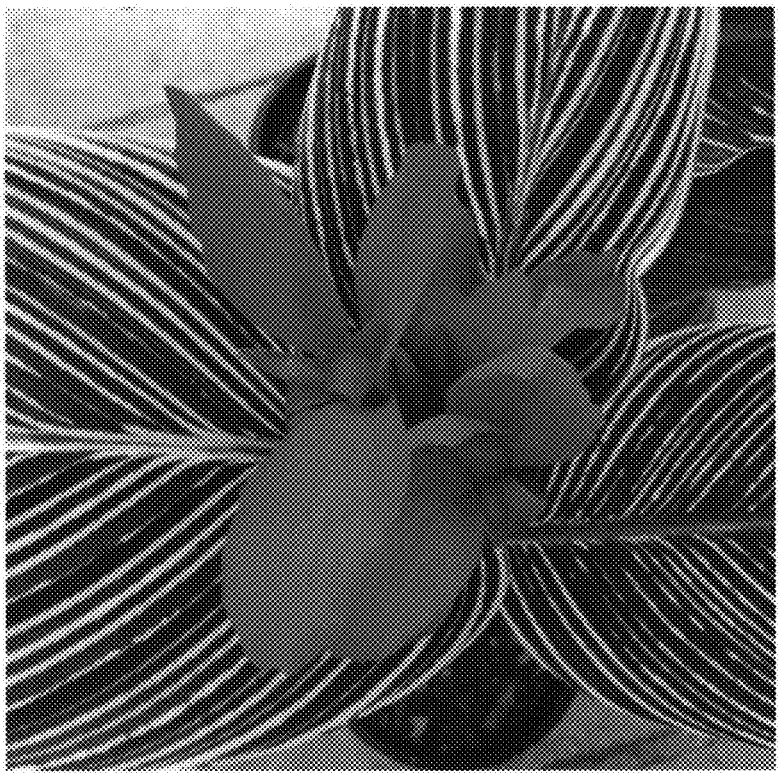

The photograph in FIG. 2 provides a close-up top view of an inflorescence and the foliage of 'Red Tiger'.

Figure 3:
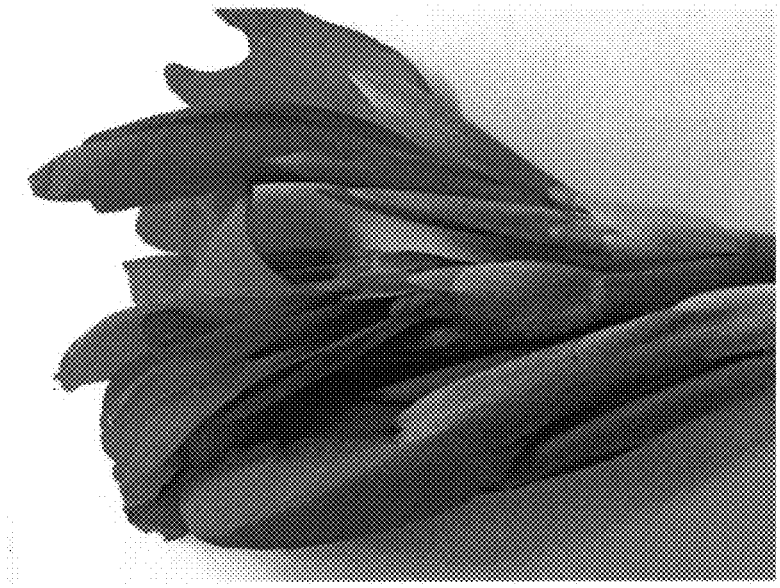

The photograph in FIG. 3 provides a close-up side view of an inflorescence with flowers beginning to open.

The colors in the photographs are as close as possible with the photographic and printing technology utilized and the color values cited in the Detailed Botanical Description accurately describe the colors of the new *Canna*.

DETAILED BOTANICAL DESCRIPTION OF THE PLANT

The following is a detailed description of one-year-old plants of the new cultivar as grown in 2-gallon containers under 6 mm poly and natural lighting in Louisville, Ky. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Blooms during active growth in summer in Louisville, Ky.

*Plant type.*—Deciduous, tropical, perennial often grown as an annual in cold climates.

*Plant habit.*—Upright and compact.

*Height and spread.*—Mid-sized; reaches 65 to 70 cm in height and about 30 cm in width as grown as a 1-year-old plant in a 2-gallon container. Reaches about 1 m in height when grown in the landscape.

*Hardiness.*—U.S.D.A. Zones 8a to 12.

*Heat tolerance.*—Observed to by highly tolerant when grown with sufficient soil moisture.

*Diseases and pests.*—No susceptibility to diseases or pests has been observed.

*Roots.*—Fleshy.

*Propagation type.*—Rhizome division.

*Growth rate.*—Vigorous, numerous suckers produced, average of 30 per 5-gallon container.

*Root development.*—Roots develop in 10 days in a stage 3 rooting media, fully develop in a 1-inch liner in 42 days, 1-inch liner fully develops in a 6-inch pot in 6 to 8 weeks.

Stem description:

*Stem size.*—An average of 38 cm in length and an average of 3 cm in width (with sheaths).

*Stem type.*—Stout, rounded, surrounded by sheathed leaf petioles.

*Stem color.*—N144A.

*Stem surface.*—Smooth and glossy.

Foliage description:

*Leaf shape.*—Broadly ovate.

*Leaf division.*—Simple.

*Leaf base.*—Cuneate.

*Leaf apex.*—Acuminate.

*Leaf venation.*—Pinnate, matching leaf color, middle raised vein 145A in color.

*Leaf margins.*—Entire, slightly wavy.

*Leaf attachment.*—Petiolate.

*Leaf arrangement.*—Alternate with petioles sheathed.

*Leaf surface.*—Glabrous on upper surface and lower surface with a slight sheen on both surfaces on newer leaves.

*Leaf orientation.*—Emerge upright and become nearly horizontal and slightly upright when mature.

*Leaf color.*—Young inner and outer surface; striped variegation a blend of 144A and 145C, mature foliage upper and lower surface; intensely variegated with thin stripes pinnately radiating in numerous colors, brightly colored stripes 150A (an average of 1 mm in width) are separated by dark green stripes 137A (of various widths ranging from 1 to 5 mm).

*Leaf size.*—Average of 25 cm in length and 17 cm in width when mature.

*Leaf quantity.*—An average of 8 per shoot.

*Petioles.*—About 15 cm in length, an average of 1 mm in width, glabrous, smooth and slightly shiny, inner and outer surface, sulcate and clasping to stem the entire length, color inner surface; 145A, outer surface; a blend of 145C and 144A.

Inflorescence description:

*Inflorescence type.*—Terminal raceme that elongates as individual flowers open; flowers with showy staminodes that are arranged spirally along the rachis and open sequentially during the bloom season.

*Inflorescence size.*—Average of 11 cm in length and 6 cm in diameter (dependent on number of blooms open).

*Flower buds.*—Linear to slightly narrow oblanceolate in shape, an average of 4.5 cm in length and 5 mm in width, color; matches sepal color when petals are unexposed, with petals slightly exposed 45B.

*Flower fragrance.*—None detected.

*Lastingness of inflorescence.*—Inflorescence blooms continuously during the bloom period, individual flowers last about 2 days.

*Flower quantity.*—Continuously produced throughout the bloom season, one to three open at one time, an average of 50 flowers produced in a season.

*Flower type.*—Comprised of less showy sepals and petals and showy staminodes.

*Flower size.*—Average of 9 cm in length, 6 cm in width.

*Rachis.*—Average of 15 cm in length and 5 mm in diameter, 146A flushed with 185A in color, glabrous surface, shape is round and becoming flattened on one side near apex, an average of 4 bracts; an average of 8 cm in length and 3 cm in width, curled inward, glabrous on both surfaces, clasping base, apex acuminate with small mucronate tip, 144A flushed with 185A.

*Sepals.*—3, lanceolate in shape, truncate base, acuminate apex, about 5 cm in length and 9 mm in width, both surfaces glabrous and shiny, both surfaces 142A in color.

*Petals.*—3, lanceolate to slightly orbicular in shape, truncate base, acute apex, about 6 cm in length and 2 mm in width, young color both surfaces; 142A, maturing color fading both surfaces; 1C and translucent, changing to fully mature color both surfaces; 185A, both surfaces glabrous and satiny, held mostly upright.

*Pedicels.*—Stout, 2 cm in length and 4 mm in width, glabrous and shiny surface, 144B in color.

*Staminodes.*—Sterile; 4, size; an average of 9.9 cm in length and 4.6 cm in width, obovate-elliptic in shape, apex round to pointed, base cuneate to narrower base about 2 cm in length and 1 cm in width with truncate base, margins slightly crenate (irregular) and wavy, color upper and lower surface; 45B in color, base spotted with 162C.

Reproductive organs:

*Gynoecium.*—1 pistil, style is an average of 7.5 cm in length and 1 cm in width, narrowly club shaped, truncate base, margins smooth, color upper and lower surface; a blend 46B, glossy on upper and lower surface, stigma surrounds apex, is about 5 mm in length and 46B in color, ovary is inferior, about 6 mm in length and 3 mm in width, and 146C in color.

*Androecium.*—1 stamen, about 3 cm in length, filament is adnate to edge of staminode, 202A and 161C in color, about 3 cm in length, anthers are about 1.5 cm in length, slightly curved, a blend of 46B and 161C in color and basifixed, pollen is moderate in quantity and 11A in color.

*Fruit and seed.*—Fruit; globose, tri-rounded pod sections, 144A in color, spiky surface very densely covered with single narrow, oblong, transparent fruits closest to 145A in color, minute in size, about 0.5 mm in length, seed; an average of 8 seeds per section, an average total of 24 total, round in shape, shiny and smooth surface, N199B.

It is claimed:

1. A new and distinct cultivar of *Canna* plant named 'Red Tiger' as herein illustrated and described.

* * * * *